(12) United States Patent
McGuckin, Jr. et al.

(10) Patent No.: US 7,097,635 B2
(45) Date of Patent: Aug. 29, 2006

(54) GUIDEWIRE RETRIEVAL MEMBER FOR CATHETER INSERTION

(75) Inventors: James F. McGuckin, Jr., Radnor, PA (US); Michael W. Paris, Hatfield, PA (US); Paul Tashjian, King of Prussia, PA (US); Peter W. J. Hinchliffe, Campbell, NY (US)

(73) Assignee: Rex Medical, L.P., Conshohocken, PA (US)

( * ) Notice: Subject to any disclaimer, the term of this patent is extended or adjusted under 35 U.S.C. 154(b) by 607 days.

(21) Appl. No.: 10/288,788

(22) Filed: Nov. 6, 2002

(65) Prior Publication Data

US 2003/0093090 A1    May 15, 2003

Related U.S. Application Data

(63) Continuation-in-part of application No. 10/279,468, filed on Oct. 24, 2002, which is a continuation-in-part of application No. 10/025,506, filed on Dec. 19, 2001, now Pat. No. 6,814,718.

(60) Provisional application No. 60/260,592, filed on Jan. 9, 2001.

(51) Int. Cl.
*A61M 5/178* (2006.01)

(52) U.S. Cl. .................................. 604/164.09

(58) Field of Classification Search ................ 600/585; 604/27, 43, 44, 164.01, 164.09, 164.13, 264, 604/272, 523
See application file for complete search history.

(56) References Cited

U.S. PATENT DOCUMENTS

| | | | |
|---|---|---|---|
| 1,248,492 A | 12/1917 | Hill | |
| 2,024,982 A | 12/1935 | Scott | |
| 2,460,473 A | 2/1949 | Larkin et al. | |
| 3,336,927 A | 8/1967 | Klebanoff | |
| 3,680,562 A | 8/1972 | Wittes et al. | |
| 3,833,003 A | 9/1974 | Tarricco | |
| 3,938,530 A | 2/1976 | Santomieri | |
| 4,134,402 A | 1/1979 | Mahurkar | |
| 4,270,535 A | 6/1981 | Bogue et al. | |
| 4,299,228 A | 11/1981 | Peters | |
| 4,345,602 A | 8/1982 | Yoshimura | |
| 4,403,983 A | 9/1983 | Edelman et al. | |
| 4,406,656 A | 9/1983 | Hattler et al. | |
| 4,431,426 A | 2/1984 | Groshong et al. | |
| 4,432,752 A | 2/1984 | Marlon | |
| 4,451,252 A | 5/1984 | Martin | |
| 4,479,792 A | 10/1984 | Lazarus et al. | |

(Continued)

FOREIGN PATENT DOCUMENTS

EP    0301854    2/1989

(Continued)

OTHER PUBLICATIONS

Moureau, Modified Seldinger Insertion Technique for PICC Insertion: The New Wave for Nurses.

(Continued)

*Primary Examiner*—Sharon Kennedy
(74) *Attorney, Agent, or Firm*—Neil D Gershon

(57) ABSTRACT

An apparatus for passing a guidewire through a subcutaneous tissue tunnel to enable over-the wire insertion of a catheter through the tissue tunnel. The apparatus comprises an elongated member having a distal end portion having a tip configured to advance through the tissue tunnel and an opening extending longitudinally with respect to the apparatus and dimensioned to receive the guidewire. The guidewire is inserted through the opening to pass the guidewire through the tunnel to enable subsequent insertion of the catheter.

15 Claims, 13 Drawing Sheets

U.S. PATENT DOCUMENTS

| | | |
|---|---|---|
| 4,490,136 A | 12/1984 | Ekbladh et al. |
| 4,493,696 A | 1/1985 | Uldall |
| 4,543,087 A | 9/1985 | Sommercorn et al. |
| 4,545,373 A | 10/1985 | Christoudias |
| 4,568,329 A | 2/1986 | Mahurkar |
| 4,574,806 A | 3/1986 | McCarthy |
| 4,581,012 A | 4/1986 | Brown et al. |
| 4,583,968 A | 4/1986 | Mahurkar |
| 4,619,643 A | 10/1986 | Bai |
| 4,623,327 A | 11/1986 | Mahurkar |
| 4,643,711 A | 2/1987 | Bates |
| 4,668,221 A | 5/1987 | Luther |
| 4,670,009 A | 6/1987 | Bullock |
| 4,682,978 A | 7/1987 | Martin |
| 4,717,379 A | 1/1988 | Ekholmer |
| 4,738,667 A | 4/1988 | Galloway |
| 4,769,016 A | 9/1988 | Labianca |
| 4,776,841 A | 10/1988 | Catalano |
| 4,808,155 A | 2/1989 | Mahurkar |
| 4,808,163 A | 2/1989 | Laub |
| 4,832,687 A | 5/1989 | Smith |
| 4,842,582 A | 6/1989 | Mahurkar |
| 4,894,057 A | 1/1990 | Howes |
| 4,895,561 A | 1/1990 | Mahurkar |
| 4,927,418 A | 5/1990 | Dake et al. |
| 4,950,259 A | 8/1990 | Geary et al. |
| 4,961,809 A | 10/1990 | Martin |
| 4,968,307 A | 11/1990 | Dake et al. |
| 4,994,027 A | 2/1991 | Farrell |
| 5,009,636 A | 4/1991 | Wortley et al. |
| 5,021,044 A | 6/1991 | Sharkawy |
| 5,053,004 A | 10/1991 | Markel et al. |
| 5,053,023 A | 10/1991 | Martin |
| 5,057,073 A | 10/1991 | Martin |
| 5,057,075 A | 10/1991 | Moncrief et al. |
| 5,059,170 A | 10/1991 | Cameron |
| 5,098,413 A | 3/1992 | Trudell et al. |
| 5,122,125 A | 6/1992 | Deuss |
| 5,135,599 A | 8/1992 | Martin et al. |
| 5,139,486 A | 8/1992 | Moss |
| 5,156,592 A | 10/1992 | Martin et al. |
| 5,167,623 A | 12/1992 | Cianci et al. |
| 5,171,216 A | 12/1992 | Dasse et al. |
| 5,195,962 A | 3/1993 | Martin et al. |
| 5,207,648 A | 5/1993 | Gross |
| 5,207,650 A | 5/1993 | Martin |
| 5,209,723 A | 5/1993 | Twardowski et al. |
| 5,209,742 A | 5/1993 | Venema et al. |
| 5,213,111 A | 5/1993 | Cook |
| 5,215,527 A | 6/1993 | Beck et al. |
| 5,221,255 A | 6/1993 | Mahurkar et al. |
| 5,221,256 A | 6/1993 | Mahurkar |
| 5,234,438 A | 8/1993 | Semrad |
| 5,246,430 A | 9/1993 | MacFarlane |
| 5,273,527 A | 12/1993 | Schatz et al. |
| 5,279,596 A | 1/1994 | Castaneda et al. |
| 5,346,471 A | 9/1994 | Raulerson |
| 5,348,536 A | 9/1994 | Young et al. |
| 5,350,358 A | 9/1994 | Martin |
| 5,360,397 A | 11/1994 | Pinchuk |
| 5,364,344 A | 11/1994 | Beattie et al. |
| 5,374,245 A | 12/1994 | Mahurkar |
| 5,378,230 A | 1/1995 | Mahurkar |
| 5,380,276 A | 1/1995 | Miller et al. |
| 5,380,290 A | 1/1995 | Makower et al. |
| 5,382,238 A | 1/1995 | Abrahamson et al. |
| 5,395,316 A | 3/1995 | Martin |
| 5,403,291 A | 4/1995 | Abrahamson |
| 5,405,320 A | 4/1995 | Twardowski et al. |
| 5,405,341 A | 4/1995 | Martin |
| 5,431,661 A | 7/1995 | Koch |
| 5,451,206 A | 9/1995 | Young |
| 5,468,159 A | 11/1995 | Brodsky |
| 5,472,417 A | 12/1995 | Martin et al. |
| 5,480,380 A | 1/1996 | Martin |
| 5,486,159 A | 1/1996 | Mahurkar |
| 5,489,278 A | 2/1996 | Abrahamson |
| 5,509,897 A | 4/1996 | Twardowski et al. |
| 5,509,900 A | 4/1996 | Kirkman |
| 5,542,925 A | 8/1996 | Orth |
| 5,556,390 A | 9/1996 | Hicks |
| 5,569,182 A | 10/1996 | Twardowski et al. |
| 5,571,093 A | 11/1996 | Cruz et al. |
| 5,662,606 A | 9/1997 | Cimino et al. |
| 5,693,030 A | 12/1997 | Lee et al. |
| 5,713,849 A | 2/1998 | Bosma et al. |
| 5,718,678 A | 2/1998 | Fleming, III |
| 5,752,939 A | 5/1998 | Makoto |
| 5,792,123 A | 8/1998 | Ensminger |
| 5,797,869 A | 8/1998 | Leblanc et al. |
| 5,807,311 A | 9/1998 | Palestrant |
| 5,807,329 A | 9/1998 | Gelman |
| 5,810,789 A | 9/1998 | Powers et al. |
| 5,830,196 A | 11/1998 | Hicks |
| 5,882,347 A | 3/1999 | Mouris-Laan et al. |
| 5,911,715 A | 6/1999 | Berg et al. |
| 5,913,848 A | 6/1999 | Luther et al. |
| 5,916,208 A | 6/1999 | Luther et al. |
| 5,919,160 A | 7/1999 | Sanfilippi |
| 5,944,732 A | 8/1999 | Raulerson et al. |
| 5,947,953 A | 9/1999 | Ash et al. |
| 5,957,893 A | 9/1999 | Luther et al. |
| 5,961,486 A | 10/1999 | Twardowski et al. |
| 5,976,103 A | 11/1999 | Martin |
| 5,976,120 A | 11/1999 | Chow et al. |
| 5,984,908 A | 11/1999 | Davis et al. |
| 5,989,206 A | 11/1999 | Prosl et al. |
| 6,001,079 A | 12/1999 | Pourchez |
| 6,036,654 A | 3/2000 | Quinn et al. |
| 6,059,771 A | 5/2000 | Balbierz et al. |
| 6,106,540 A | 8/2000 | White et al. |
| 6,120,494 A | 9/2000 | Jonkman |
| 6,126,631 A | 10/2000 | Loggie |
| 6,132,405 A | 10/2000 | Nilsson et al. |
| 6,146,354 A | 11/2000 | Beil |
| 6,146,373 A | 11/2000 | Cragg et al. |
| 6,152,909 A | 11/2000 | Bagaoisan et al. |
| 6,156,016 A | 12/2000 | Maginot |
| 6,180,059 B1 | 1/2001 | Divino, Jr. et al. |
| 6,190,349 B1 | 2/2001 | Ash et al. |
| 6,190,371 B1 | 2/2001 | Maginot et al. |
| 6,193,685 B1 | 2/2001 | Goodin |
| 6,196,996 B1 | 3/2001 | Teirstein |
| 6,210,365 B1 | 4/2001 | Afzal |
| 6,223,070 B1 | 4/2001 | Chait |
| 6,264,627 B1 | 7/2001 | Liska et al. |
| 6,273,879 B1 | 8/2001 | Keith et al. |
| 6,280,423 B1 | 8/2001 | Davey et al. |
| 6,293,927 B1 | 9/2001 | McGuckin, Jr. |
| 6,293,958 B1 | 9/2001 | Berry et al. |
| 6,296,631 B1 | 10/2001 | Chow |
| 6,328,730 B1 | 12/2001 | Harkrider, Jr. |
| 6,358,229 B1 | 3/2002 | Tihon |
| 6,361,529 B1 | 3/2002 | Goodin et al. |
| 6,394,141 B1 | 5/2002 | Wages et al. |
| 6,454,997 B1 | 9/2002 | Divino, Jr. et al. |
| 6,638,242 B1 | 10/2003 | Wilson et al. |
| 6,786,884 B1 | 9/2004 | DeCant, Jr. et al. |
| 6,890,321 B1 | 5/2005 | Luther et al. |
| 2002/0087145 A1 | 7/2002 | Ehwald et al. |
| 2003/0023198 A1 | 1/2003 | Twardowski |
| 2003/0088213 A1 | 5/2003 | Schwiekert |
| 2003/0153898 A1 | 8/2003 | Schon et al. |
| 2003/0204179 A1 | 10/2003 | Davey et al. |

2004/0064086 A1    4/2004    Gottlieb et al.

FOREIGN PATENT DOCUMENTS

| EP | 0440992 | 8/1991 |
| WO | WO 9737699 | 10/1997 |
| WO | WO 0176677 | 10/2001 |

OTHER PUBLICATIONS

Seldinger Technique for Introduding Catheters.
Journal of Vascular and Interventional Radiology 12:376-378 (2001), "Sheathless Technique of Ash Split-Cath Insertion", Aalpen Patel, MD, Stephen Hofkin, MD, David Ball, DO, Gary Cohen, MD and Douglas C. Smith, MD.

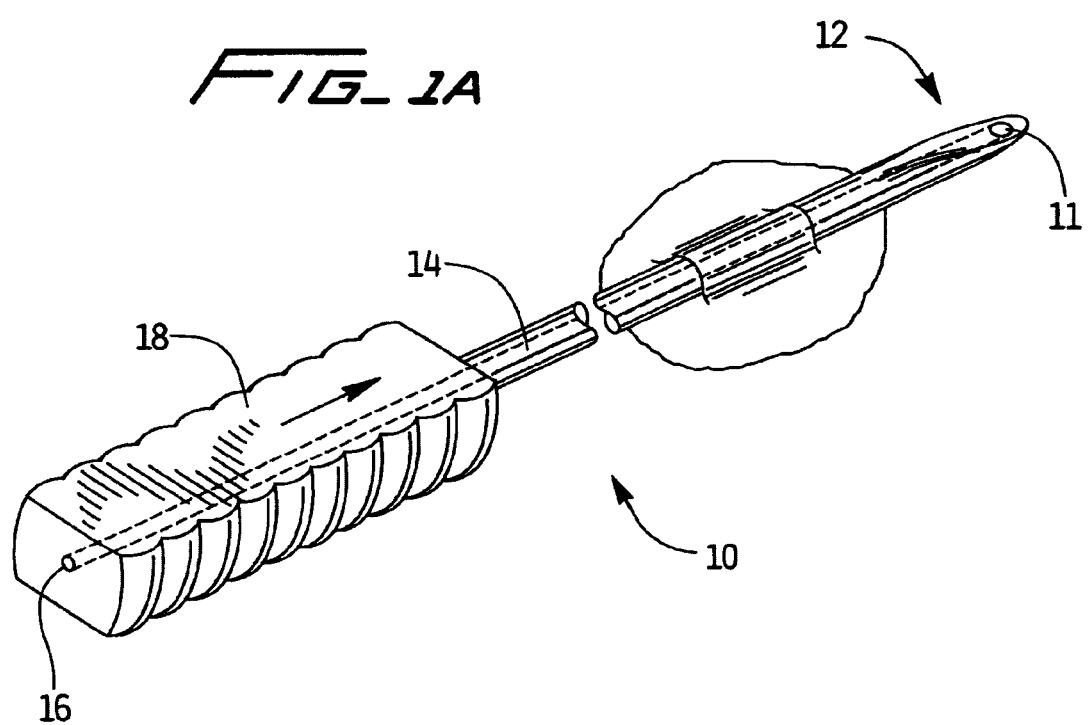

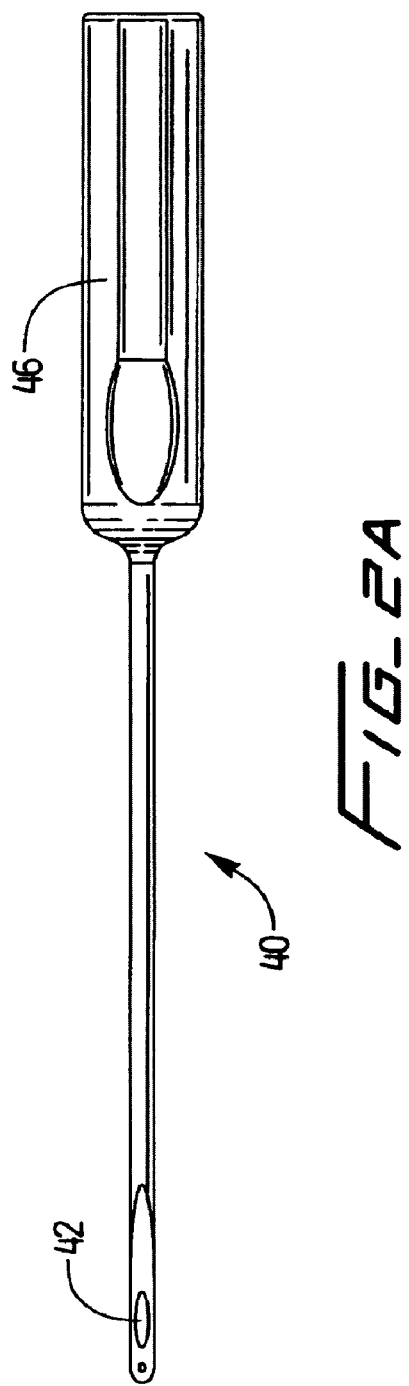
FIG_2A
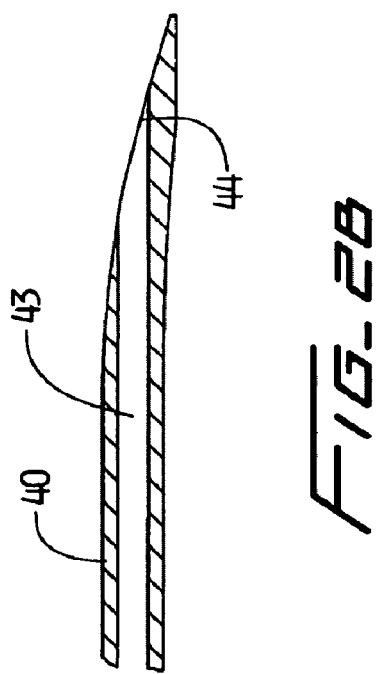
FIG_2B

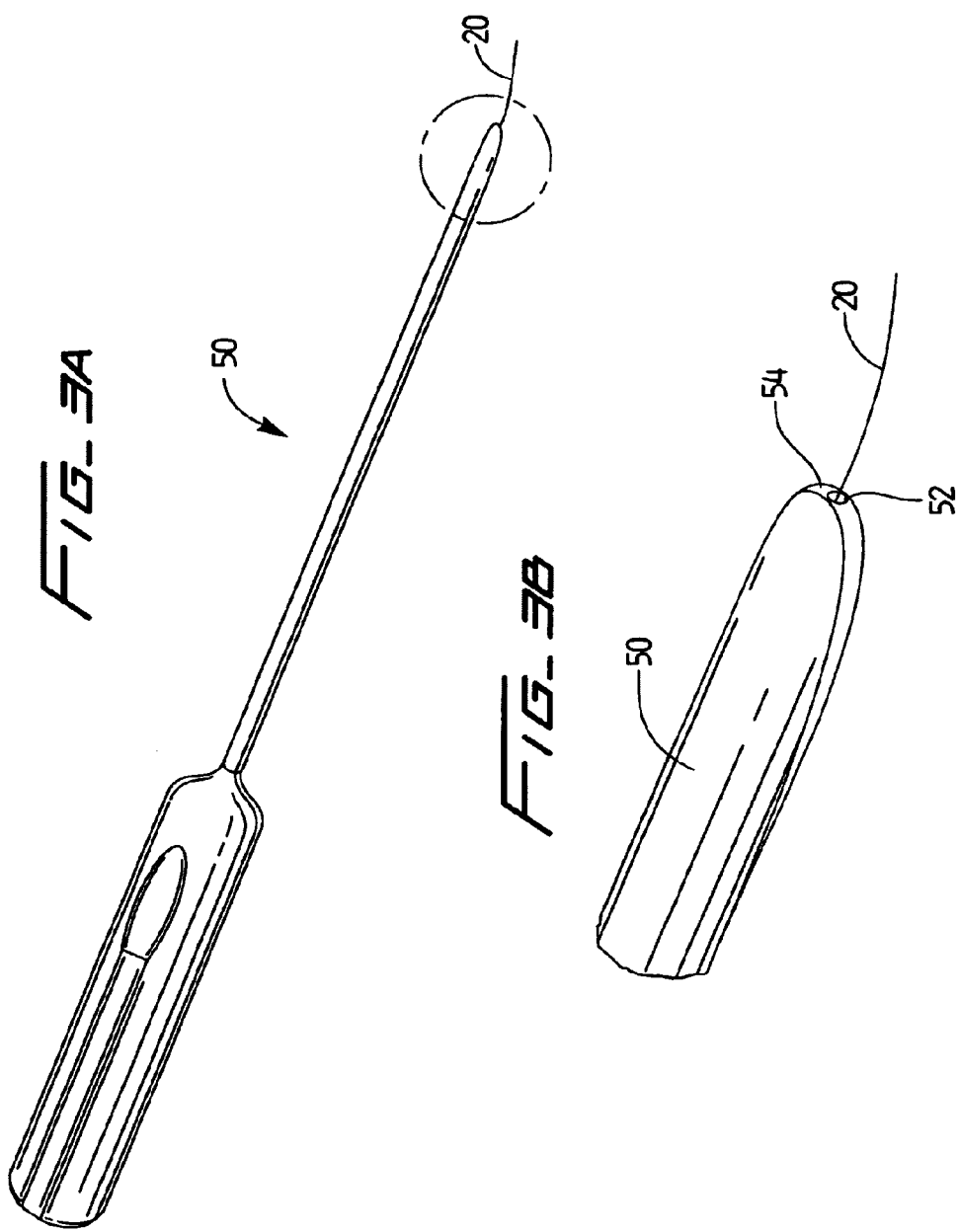

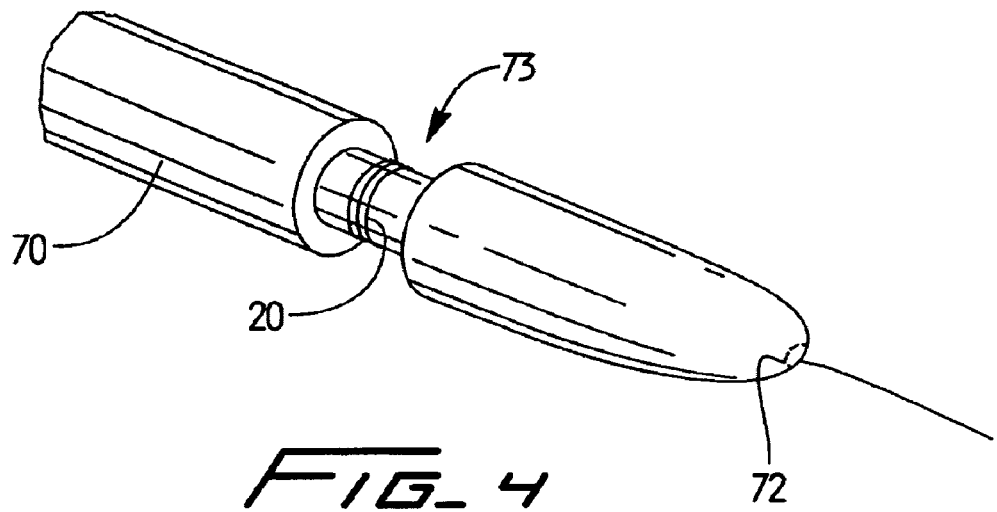
FIG_4
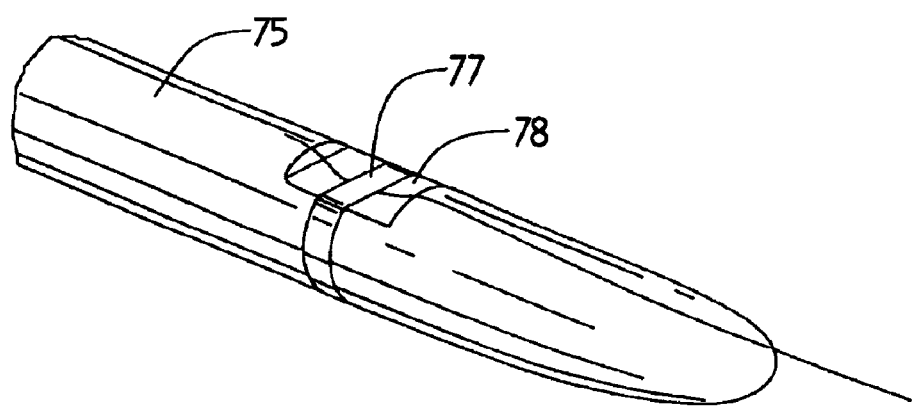
FIG_5A

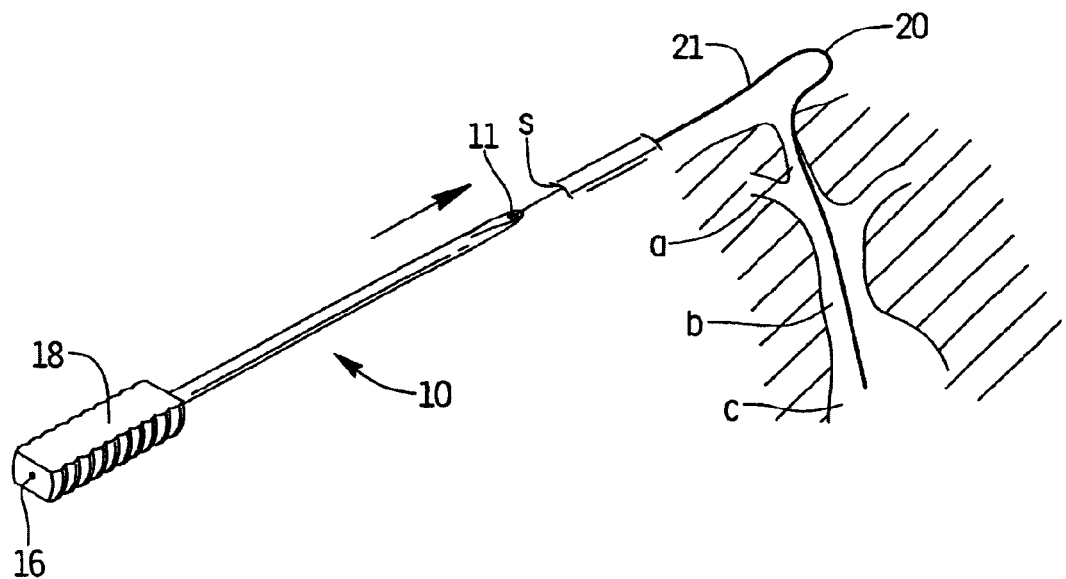
FIG_6A
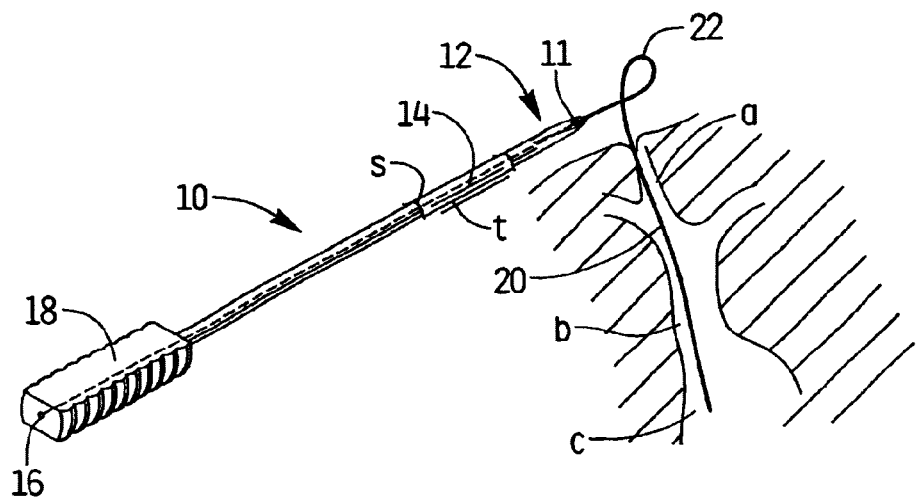
FIG_6B

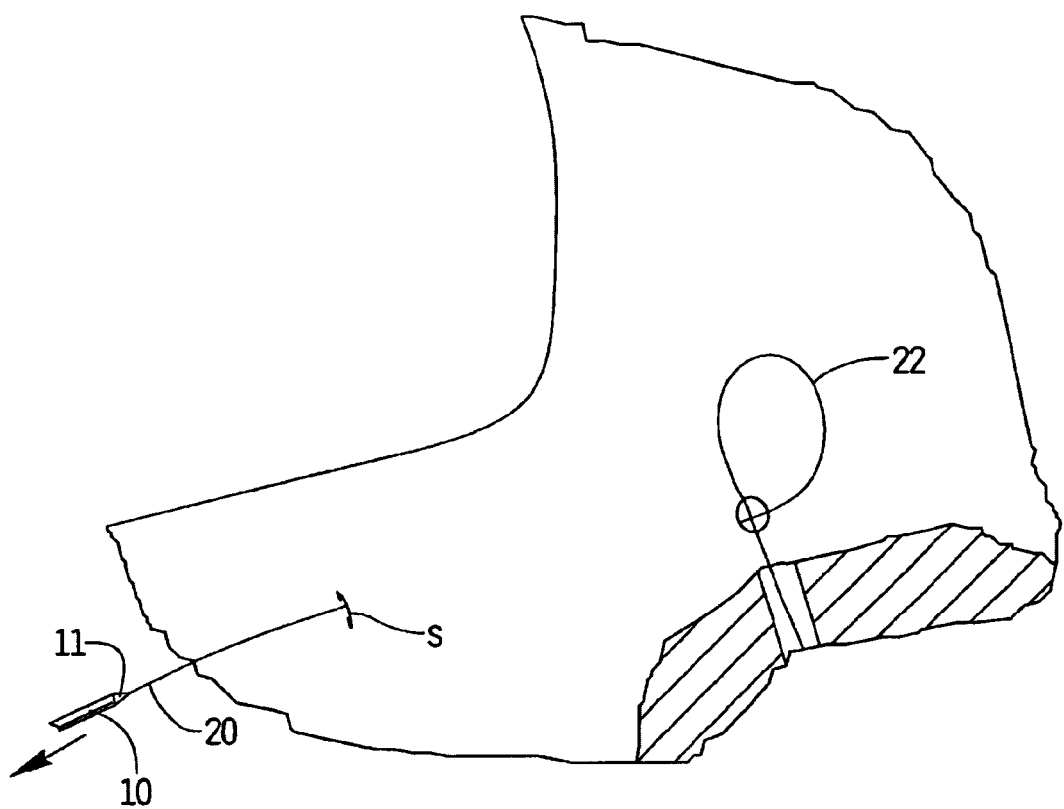
FIG_6D

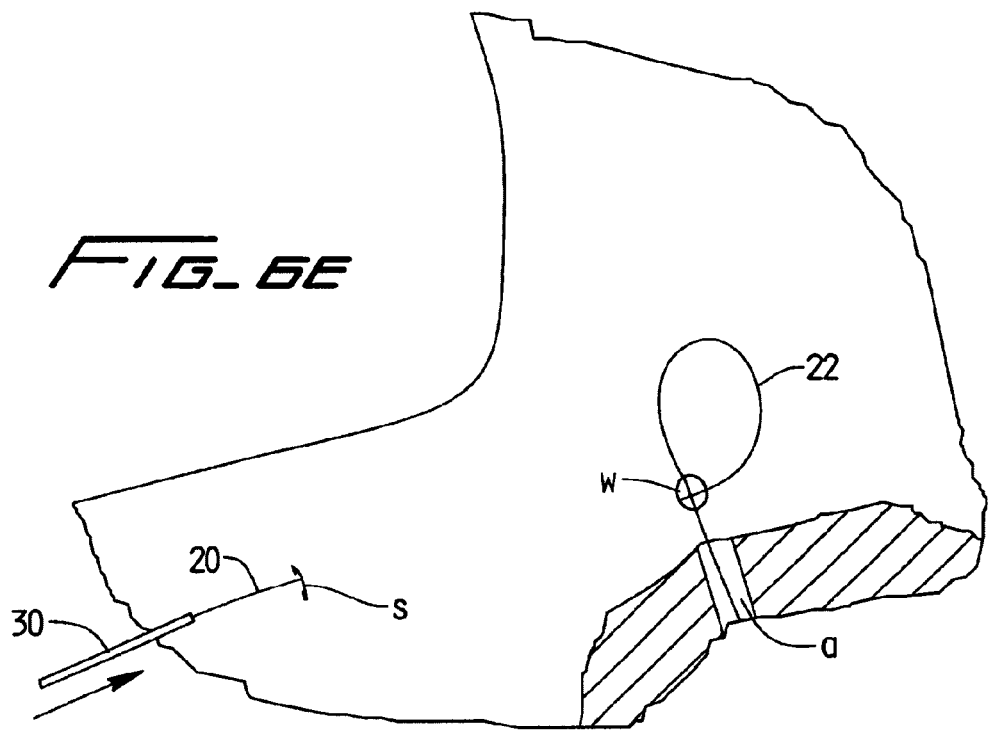
FIG_6E
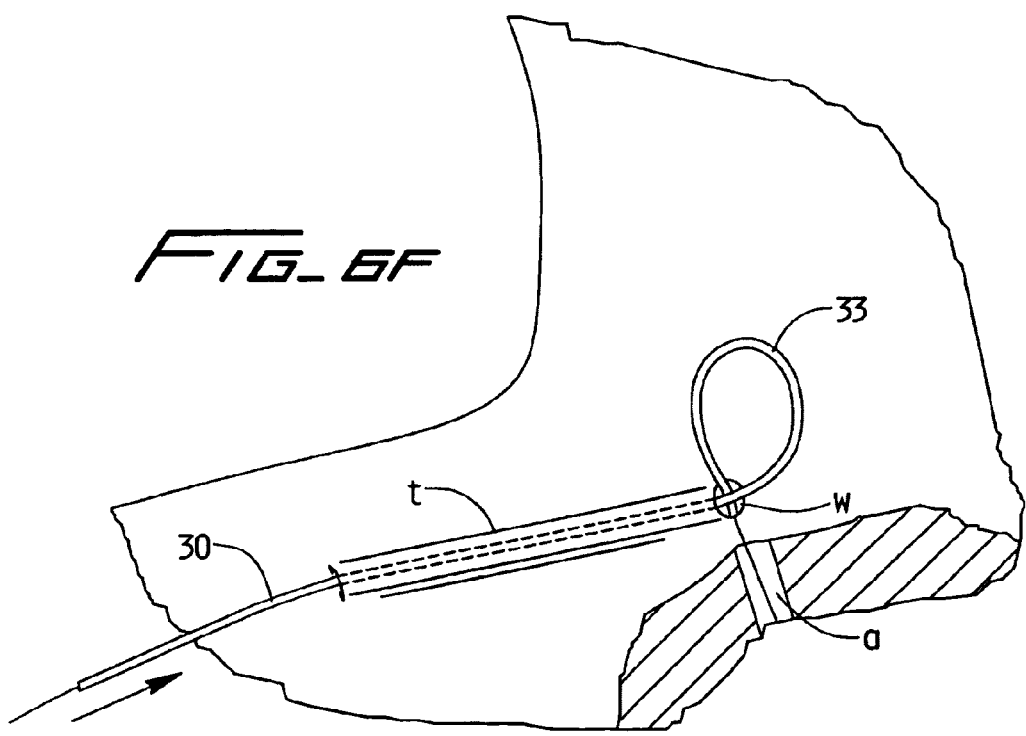
FIG_6F

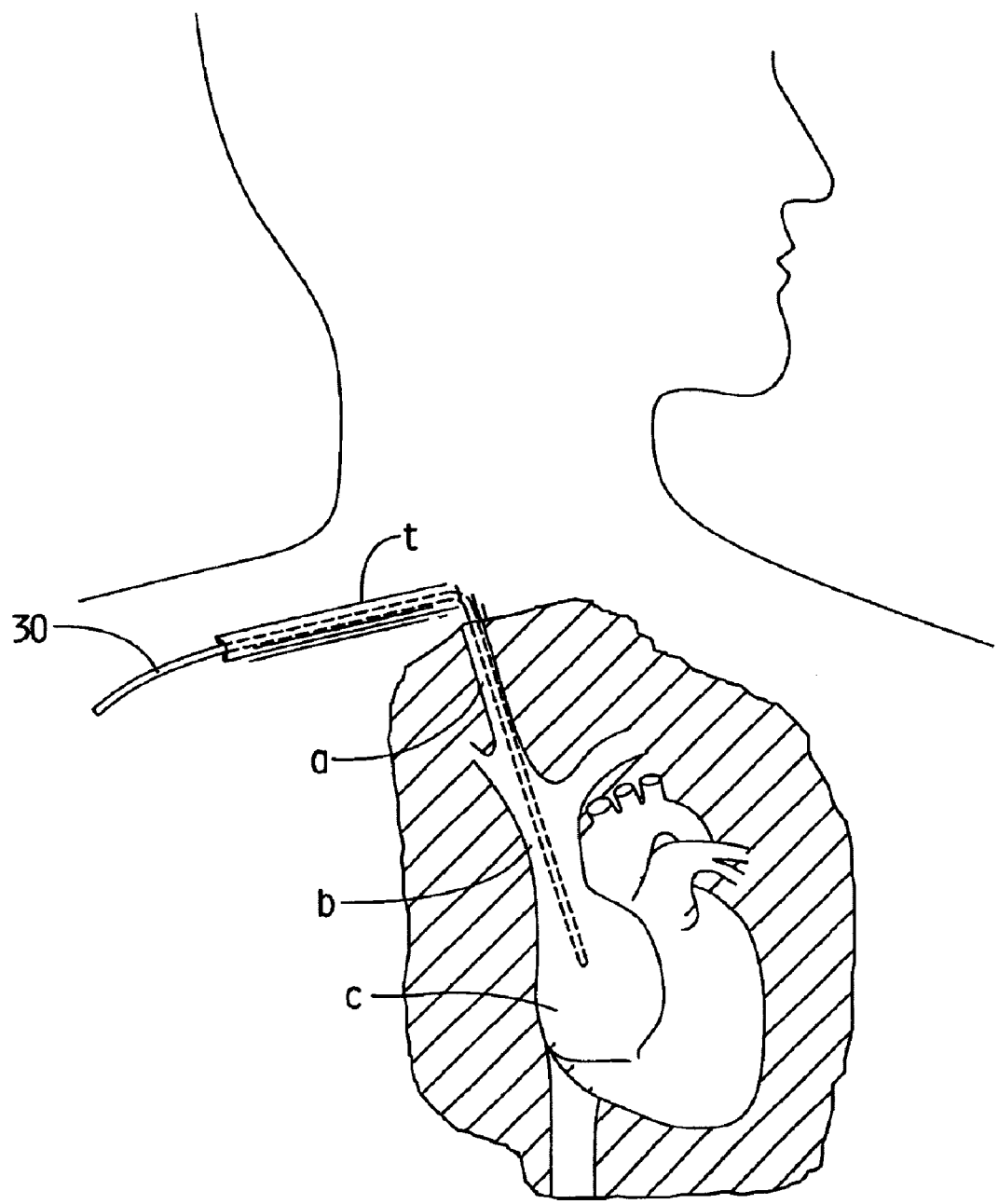
FIG_6G

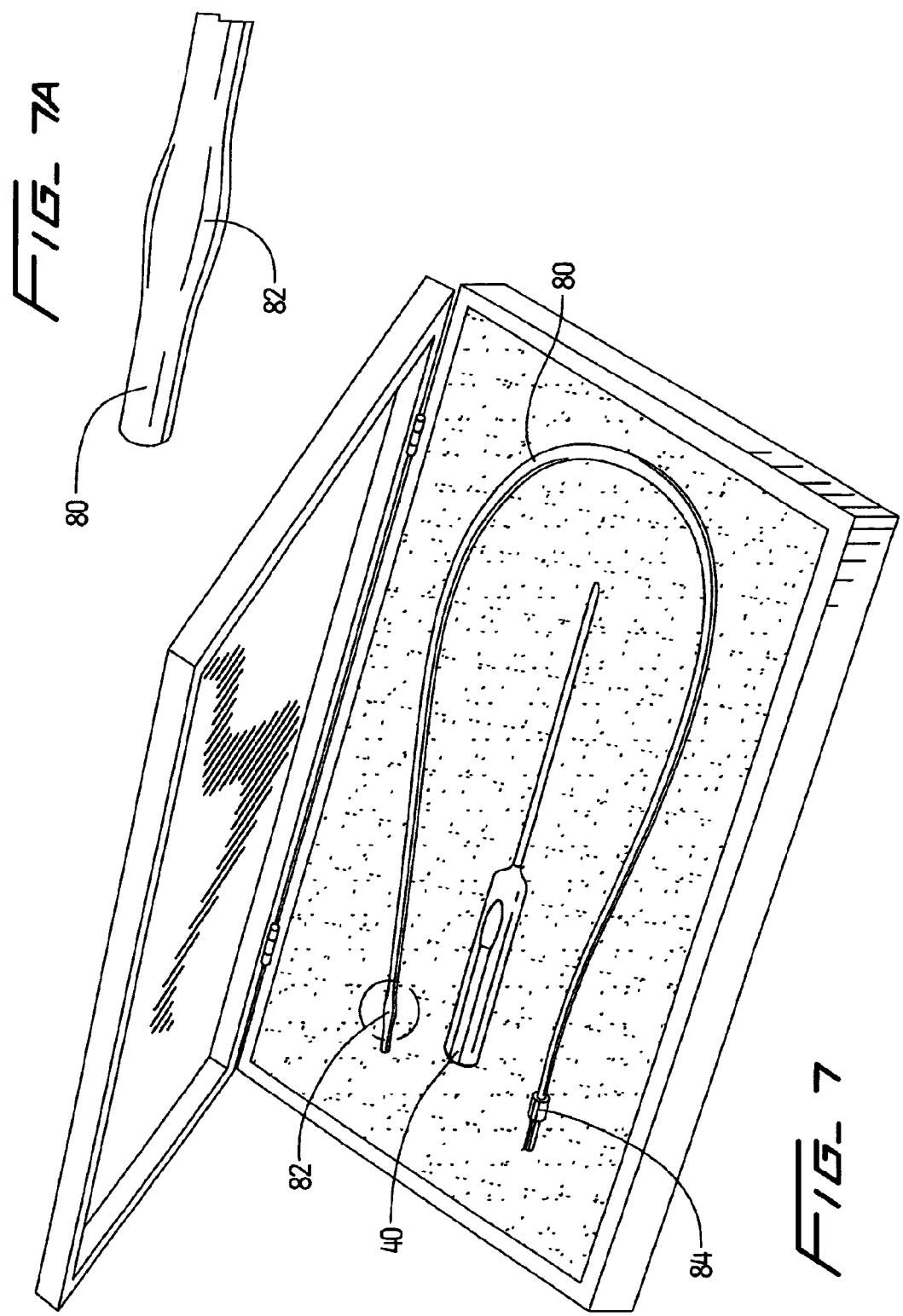

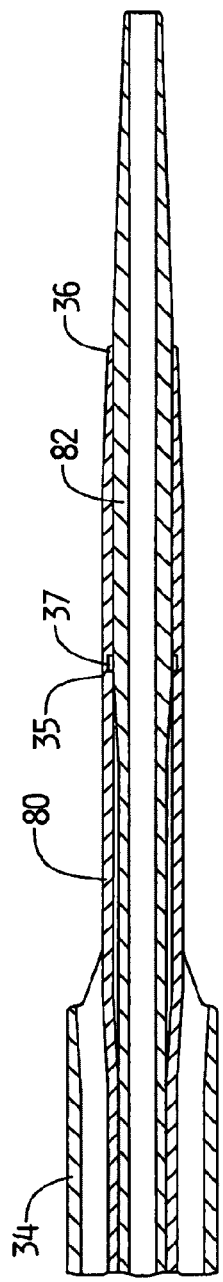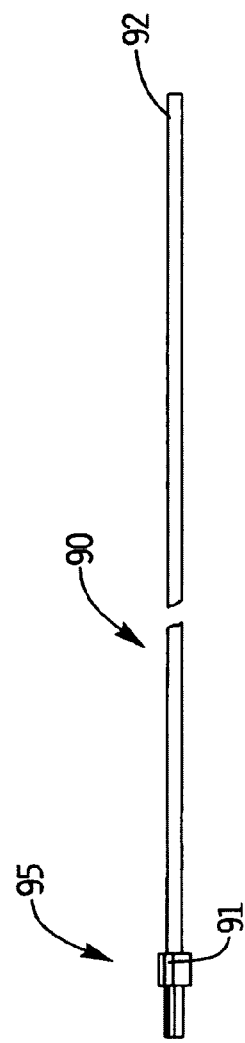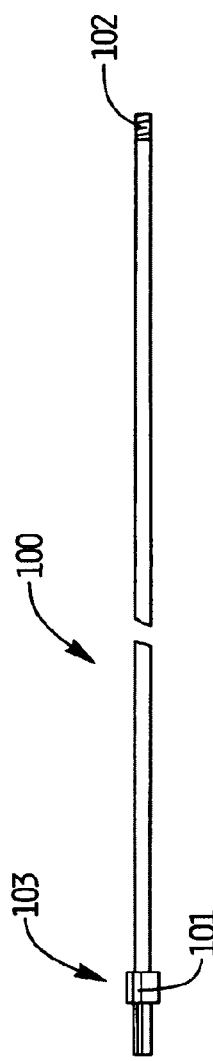

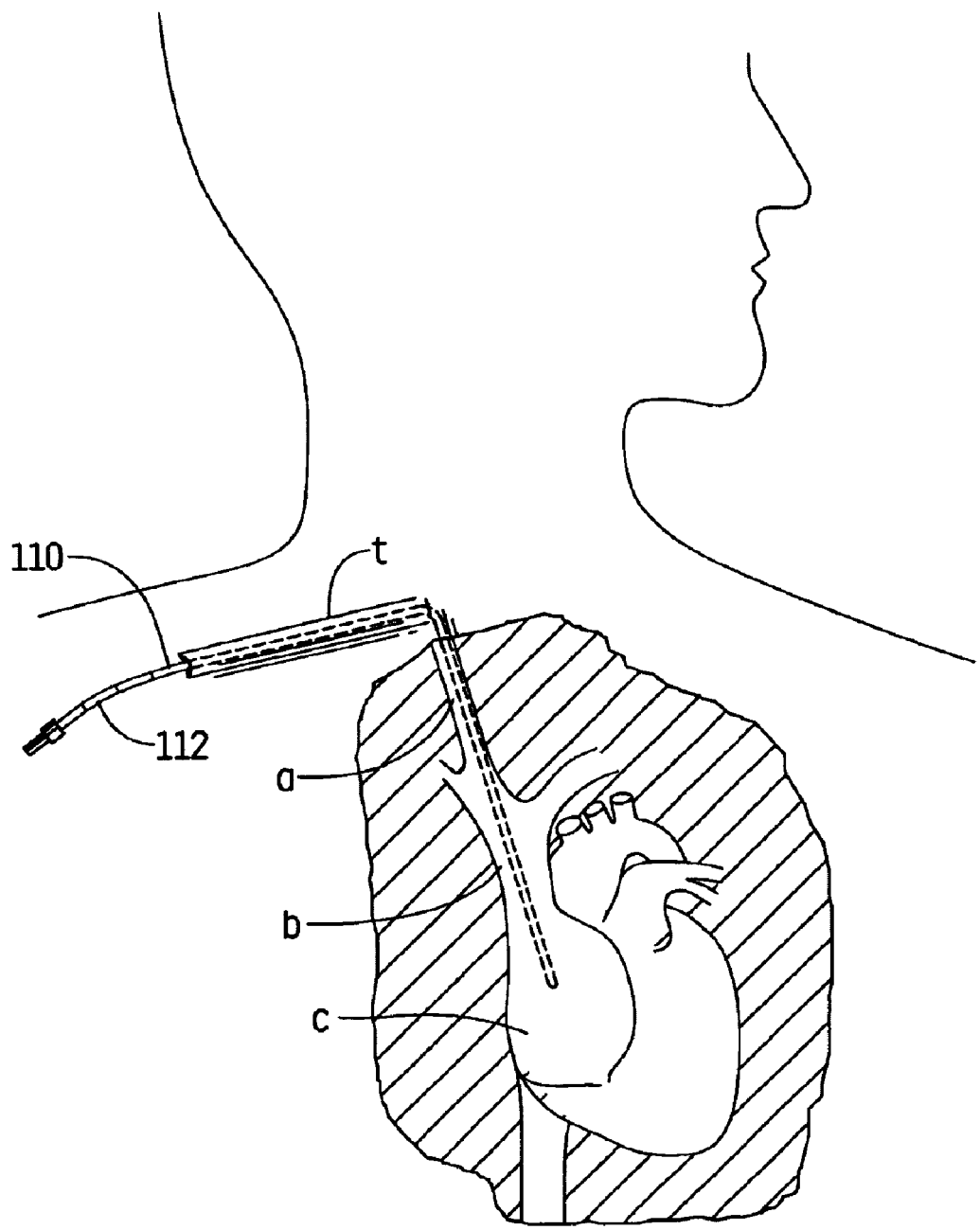
FIG_10

GUIDEWIRE RETRIEVAL MEMBER FOR CATHETER INSERTION

This application is a continuation-in-part of application Ser. No. 10/279,468 filed Oct. 24, 2002, which is a continuation-in-part of application Ser. No. 10/025,506, filed Dec. 19, 2001 now U.S. Pat. No. 6,814,718, which claims priority from provisional application Ser. No. 60/260,592, filed Jan. 9, 2001. The entire contents of these applications are incorporated herein by reference.

BACKGROUND

1. Technical Field

This application relates to an apparatus and method for guidewire retrieval for over the wire insertion of catheters.

2. Background of Related Art

Hemodialysis is a well known method of providing renal (kidney) function by circulating blood. A dialysis catheter is typically inserted through the jugular vein and maneuvered into position through the superior vena cava into the right atrium. Blood is withdrawn from the patient's body through the dialysis catheter and transported to a dialysis (kidney) machine. In the dialysis machine, the waste products are removed, and the filtered blood is returned to the patient's body through the catheter.

Prior art catheters such as the MedComp Ash Split catheter are inserted through introducer sheaths which are then manually separated (peeled) and removed from the site. These dialysis catheters require numerous steps for insertion because of the tear away sheath. The multiple insertion steps can be summarized as follows:

1. an introducer needle is inserted through a first incision site (first opening) to properly locate (access) the vessel, e.g. the right internal jugular vein;
2. a guidewire is inserted through the needle into the internal jugular vein and down through the superior vena cava into the inferior vena cava;
3. the introducer needle is withdrawn leaving the guidewire in place;
4. a tear away (peel away) sheath and dilator are inserted over the guidewire and through the first incision site to provide an access port for the dialysis catheter into the jugular vein, superior vena cava and right atrium;
5. a second incision is made in the chest wall to create a second opening;
6. a trocar is attached to the distal end of the dialysis catheter;
7. the trocar and dialysis catheter are pushed through the second incision and advanced to bluntly dissect the subcutaneous tissue to exit the first incision (opening) which was created by the introducer needle, thereby creating a subcutaneous tissue tunnel between the first and second openings;
8. the trocar is detached from the dialysis catheter leaving the catheter in place extending from the second opening, through the tissue tunnel and out the first opening;
9. the dilator and guidewire are removed, leaving the tear away sheath in place in the first incision which has been expanded by the dilator;
10. the dialysis catheter, which is protruding from the first incision, is inserted through the tear away sheath and advanced so its distal portion is positioned in the right atrium;
11. the sheath is separated, i.e. split, by pulling the tabs apart, and then pulled upwardly away from the dialysis catheter and removed from the body, leaving the catheter in place; and
12. the second incision is closed and the dialysis catheter, which is connected through tubes to the dialysis machine, is left in place an extended period of time to provide blood circulation to and from the dialysis machine.

Alternatively, in the foregoing method, the trocar can be forced through a third incision exiting adjacent the first incision, and then the catheter inserted through the second and third incisions and the introducer sheath positioned in the first incision.

This multiple step process of inserting the prior art dialysis catheter is time consuming and complicates the surgical procedure. These multiple steps also add to the cost of the procedure, not only because of the additional surgeon's time but because additional components, such as the tear-away sheath, are required which increases the overall cost of the catheter system. Also, removal of the dilator increases the tendency of the sheath to kink causing difficulties in catheter insertion.

The use of the tear away sheath is also problematic. The tear-away style sheath has lines of weakness to separate the sheath as it is pulled apart by the pull tabs for removal. However, the sheath can potentially cause damage to the vessel wall as it is being pulled apart and can cause infection. Moreover, pulling the sheath laterally can enlarge the incision, thereby increasing the difficulty of closing the incision at the end of the procedure. Also, since the sheath is pulled in the proximal direction for removal, it could pull the catheter proximally as well, thereby pulling it away from the desired site, and requiring repositioning. The edges of the tear away can also lacerate the surgeon's glove and finger. Over dilation caused by the sheath can also cause blood leakage.

An additional potential risk with utilizing tear away sheaths is that air embolism can occur. During the time the surgeon withdraws the dilator from the sheath and inserts the catheter, a passageway through the sheath to the vessel is open. If the patient inhales during this catheter exchange, an air bubble can enter the vascular system and obstruct the vessel, potentially causing stroke or even death.

It would therefore be advantageous if a dialysis catheter insertion method could be provided which reduces some of the foregoing procedural steps, thereby decreasing the complexity of the procedure and decreasing the hospital and surgeon costs. It would also be advantageous if such dialysis catheter insertion method could be provided which would be less traumatic and avoid the foregoing problems associated with the use of a tear-away sheath.

To achieve such insertion, it would be necessary to ensure the catheter has sufficient stiffness to be pushed through the subcutaneous tissue tunnel and vessels into the right atrium. However, such stiffness must not significantly reduce catheter flexibility which would render navigation of the catheter difficult and potentially traumatic to the vessels.

The need therefore exists for a dialysis catheter having the necessary stiffness, while retaining sufficient flexibility, to enable the advantageous insertion characteristics described herein, e.g. reduction of catheter insertion time, simplification of the catheter insertion process, and elimination of a peel-away introducer sheath.

The catheter and insertion methods disclosed in co-pending commonly assigned Ser. No. 10/279,468, filed Oct. 24, 2002, the contents of which is incorporated herein by reference in its entirety, satisfies the above-mentioned needs and provides the foregoing advantages by providing a complete over-the-wire catheter insertion method which eliminates the need for a peel-away sheath. As disclosed in this application, a trocar is provided for retrieving the guidewire and passing it through the tissue tunnel for subsequent guidance of the catheter. The present invention discloses various trocars for achieving placement of the guidewire through the subcutaneous tissue tunnel. Such placement of the guidewire also advantageously enables over the wire insertion of different types of catheters.

SUMMARY

The present invention provides an apparatus for passing a guidewire through a subcutaneous tissue tunnel to enable over-the wire insertion of a catheter through the tissue tunnel and into the vessel. The apparatus comprises an elongated member having a distal end portion having a tip configured to advance through the tissue tunnel and an opening extending longitudinally with respect to the apparatus and dimensioned to receive the guidewire. The guidewire is inserted through the opening to thereby pass the guidewire through the tunnel to enable subsequent insertion of the catheter over the guidewire.

In one embodiment, the opening extends from the tip of the apparatus to a proximal end portion. In one embodiment, the opening is formed in a side wall of the apparatus. In another embodiment the opening is formed in the distalmost end.

The present invention also provides an apparatus for passing a guidewire through a subcutaneous tissue tunnel to enable over-the wire insertion of a catheter through the tunnel and into the patient's vessel comprising an elongated member having a distal end portion and guidewire retaining structure. The distal end portion has a tip configured to advance through the tissue tunnel and the guidewire retaining structure engages the guidewire and retains the guidewire during movement of the apparatus through the tissue tunnel to thereby enable passage of the guidewire through the tunnel to enable subsequent insertion of the catheter over the guidewire.

In one embodiment, the guidewire retaining structure comprises a hook at the distal portion of the apparatus. In another embodiment, the guidewire retaining structure comprises a through hole in the distal end of the trocar.

In one embodiment, the apparatus comprises a trocar having a dissecting tip. In another embodiment, the apparatus comprises a dilator having a dilating tip.

The present invention also provides a system for placement of a dialysis catheter comprising a trocar and a stiffener. The trocar has a distal tip configured to dissect tissue and structure to receive a guidewire. The trocar provides passage of the guidewire through a subcutaneous tissue tunnel. The stiffener is removably insertable into a lumen of the dialysis catheter to provide increased rigidity to the catheter to enhance pushability over the guidewire through the tissue tunnel.

In one embodiment the stiffener comprises a rod having engaging structure abutting an internal wall of the catheter. The stiffener preferably includes a threaded proximal portion for releasable engagement with the dialysis catheter.

The present invention also provides a kit for inserting a dialysis catheter through a subcutaneous tissue tunnel into a patient's vessel comprising:

a guidewire passer for passing a guidewire through a subcutaneous tissue tunnel so the guidewire extends from the vessel through a proximal opening of the tunnel to enable a dialysis catheter to be inserted through the tissue tunnel over the guidewire; and a stiffener insertable into a lumen of the catheter to stiffen at least a portion of the catheter to facilitate advancement of the catheter over the guidewire through the tissue tunnel and through the vessel.

In one embodiment, the trocar of the kit includes a longitudinal passageway dimensioned to receive the guidewire. The stiffener preferably includes a threaded proximal portion for releasable engagement with the dialysis catheter. In one embodiment, the stiffener includes an abutment surface for abutment with a shoulder of the dialysis catheter. In another embodiment, the stiffener includes a protruding surface on an outer wall for engagement with the internal wall of the dialysis catheter.

A method for over the wire placement of a catheter through a subcutaneous tissue tunnel and into a vessel is also provided. The method comprises:

inserting a guidewire into the vessel so a proximal portion extends proximally of the patient's body;

providing a guidewire retrieval member;

passing the guidewire through the tissue tunnel via the guidewire retrieval member so a proximal end of the guidewire extends through a proximal opening of the tissue tunnel and outside the patient's body; and advancing a catheter over the guidewire through the subcutaneous tissue tunnel and into the patient's vessel.

The method may further comprise the step of advancing the guidewire retrieval member distally through the subcutaneous tissue tunnel prior to passing the guidewire through the tissue tunnel. The method may further include the step of threading the guidewire through a longitudinal opening in the retrieval member.

The present invention also provides a method for determining a length of catheter for insertion over a guidewire extending through a tissue tunnel and into a vessel comprising:

inserting the guidewire into the vessel so a proximal portion extends proximally of a patient's body;

passing the guidewire through the tissue tunnel so a proximal end of the guidewire extends through a proximal opening of the tissue tunnel and outside the patient's body; and advancing a device over the guidewire through the subcutaneous tissue tunnel and into the patient's vessel to determine a length of catheter.

In one embodiment the device is in the form of a dilator containing indicator markings and the step of advancing the dilator to determine the length of the catheter includes viewing the markings to provide an indicator of the length of the catheter. In another embodiment, the device is a stiffener rod containing indicator markings.

BRIEF DESCRIPTION OF THE DRAWINGS

Preferred embodiment(s) of the present disclosure are described herein with reference to the drawings wherein:

FIG. 1A is a perspective view of a first embodiment of a trocar of the present invention for passing a guidewire through the subcutaneous tissue tunnel for subsequent over the wire insertion of the dialysis catheter;

FIG. 1B is a perspective view illustrating the trocar (guidewire retrieval/passing member) of FIG. 1 being withdrawn from the tissue tunnel leaving the guidewire in place;

FIG. 2A is a bottom view of a second embodiment of the guidewire passing trocar of the present invention;

FIG. 2B is a sectional view of the distal portion of the trocar of FIG. 2A;

FIG. 3A is a top perspective view of a third embodiment of the trocar;

FIG. 3B is an enlarged view of the distal tip region of the trocar of FIG. 3A;

FIG. 4 is a perspective view of a fourth embodiment of the trocar;

FIG. 5A is a perspective view of a fifth embodiment of the trocar;

FIGS. 6A–6G are method steps showing use of the trocar of FIG. 1 to retrieve a guidewire and advance the dialysis catheter over the wire, wherein:

FIG. 6A illustrates the trocar being inserted through the tissue tunnel;

FIG. 6B illustrates the guidewire partially inserted into the trocar (a part of the tunnel has been removed so the trocar distal tip can be viewed);

FIG. 6C illustrates the guidewire extending through the trocar;

FIG. 6D illustrates the trocar withdrawn leaving the guidewire in place;

FIG. 6E illustrates the dialysis catheter being inserted over the guidewire towards the tissue tunnel;

FIG. 6F illustrates the dialysis catheter further inserted through the tissue tunnel and over the looped guidewire portion;

FIG. 6G illustrates the dialysis catheter extending through the tissue tunnel and fully inserted into the right atrium and the guidewire withdrawn;

FIG. 7 is a perspective of a kit of the present invention containing a trocar and catheter stiffening rod;

FIG. 7A is an enlarged view of a distal region of the stiffening rod of FIG. 7;

FIG. 8 illustrates a longitudinal cross-sectional view showing the stiffener rod of FIG. 7 positioned within the catheter;

FIGS. 9A and 9B illustrate alternate embodiments of the stiffener rod; and

FIG. 10 illustrates a stiffener rod having distance markings to provide an indicator for selecting a desirable length of catheter.

DETAILED DESCRIPTION OF PREFERRED EMBODIMENTS

Figure 5B:
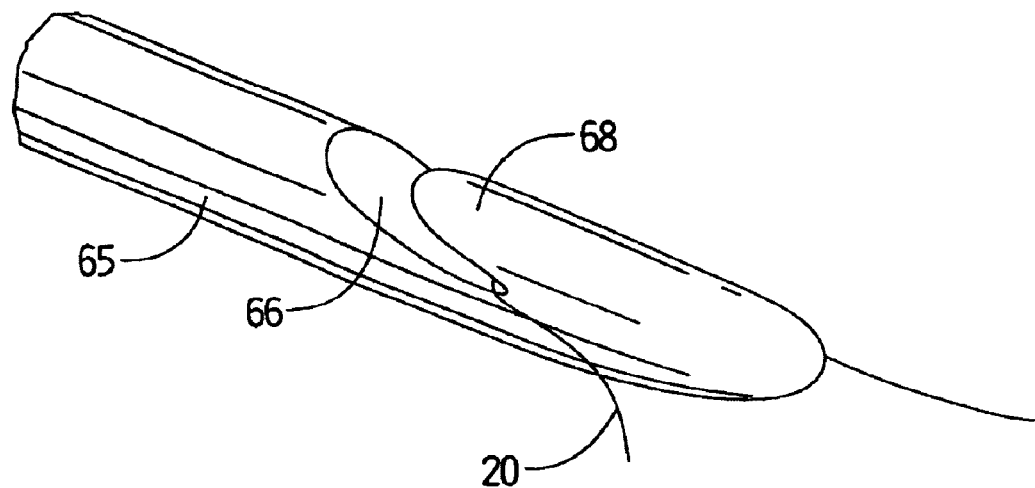
FIG. 5B is a perspective view of a sixth embodiment of the trocar.

This application discloses several embodiments of trocars (guidewire retrieval/passing members) for passing a guidewire through an already formed subcutaneous tissue tunnel. The trocars enable the guidewire, extending from the patient's vascular system, to be passed through a distal end and emerge from a proximal end of the tissue tunnel to enable subsequent over the wire insertion of a dialysis catheter through the tunnel and vascular system. The preferred types of catheters that can be inserted over the wire in this fashion are disclosed in detail in co-pending patent application Ser. No. 10/279,468 and for brevity these are not further described herein. However, it should be appreciated that other dialysis catheters, including current competitors' catheters, could potentially be modified for over the wire insertion and this is discussed in more detail below.

The method of insertion of the present invention which provides a complete over the wire system for the catheter will first be described with reference to the trocar of FIG. 1A, it being understood that various alternative guidewire retrieval or passage instruments (trocars) such as those illustrated in alternative embodiments described herein can be utilized.

Trocar 10 has a lumen 14 formed therethrough (shown in phantom in FIG. 1A) dimensioned for reception of guidewire 20. The lumen 14 extends the entire length of trocar 10, from a proximal opening 16 in handle 18 to a distal opening 11 in a wall of the catheter on the underside of the trocar as viewed in FIG. 1A. Distal opening 11 is adjacent the distal tip 12, at the region where it tapers. The blunt distal tip 12 of trocar 10 bluntly dissects tissue to create a subcutaneous tissue tunnel for subsequent securement of the catheter. Note the lumen 14 of trocar 10 can be smaller than the outer diameter of the dialysis catheter, since it only needs to have an internal diameter of about 0.040 to about 0.045 inches to receive the guidewire. The diameter of the dialysis catheter is typically about 0.170 to about 0.220 inches The preferred method of insertion will now be described in conjunction with FIGS. 6A–6G. The method will be described for inserting a dialysis catheter into the right atrium, such as the one of the dialysis catheters of the '506 application. Other placements of the catheter are also contemplated.

First, a needle (not shown) is inserted into the internal jugular vein to properly locate the vessel and a guidewire 20 is inserted through the needle into the right internal jugular vein "a" and into the superior vena cava "b". The guidewire 20 is further advanced into the right atrium "c" and preferably into the inferior vena cava. The needle is then withdrawn, leaving the guidewire 20 in place, extending out of the patient's body at the proximal portion 21 as shown in FIG. 6A. Note the guidewire 20 can be positioned to form a guidewire loop 22 (FIG. 6B) to facilitate insertion of the catheter as will be described below.

Figure 6C:
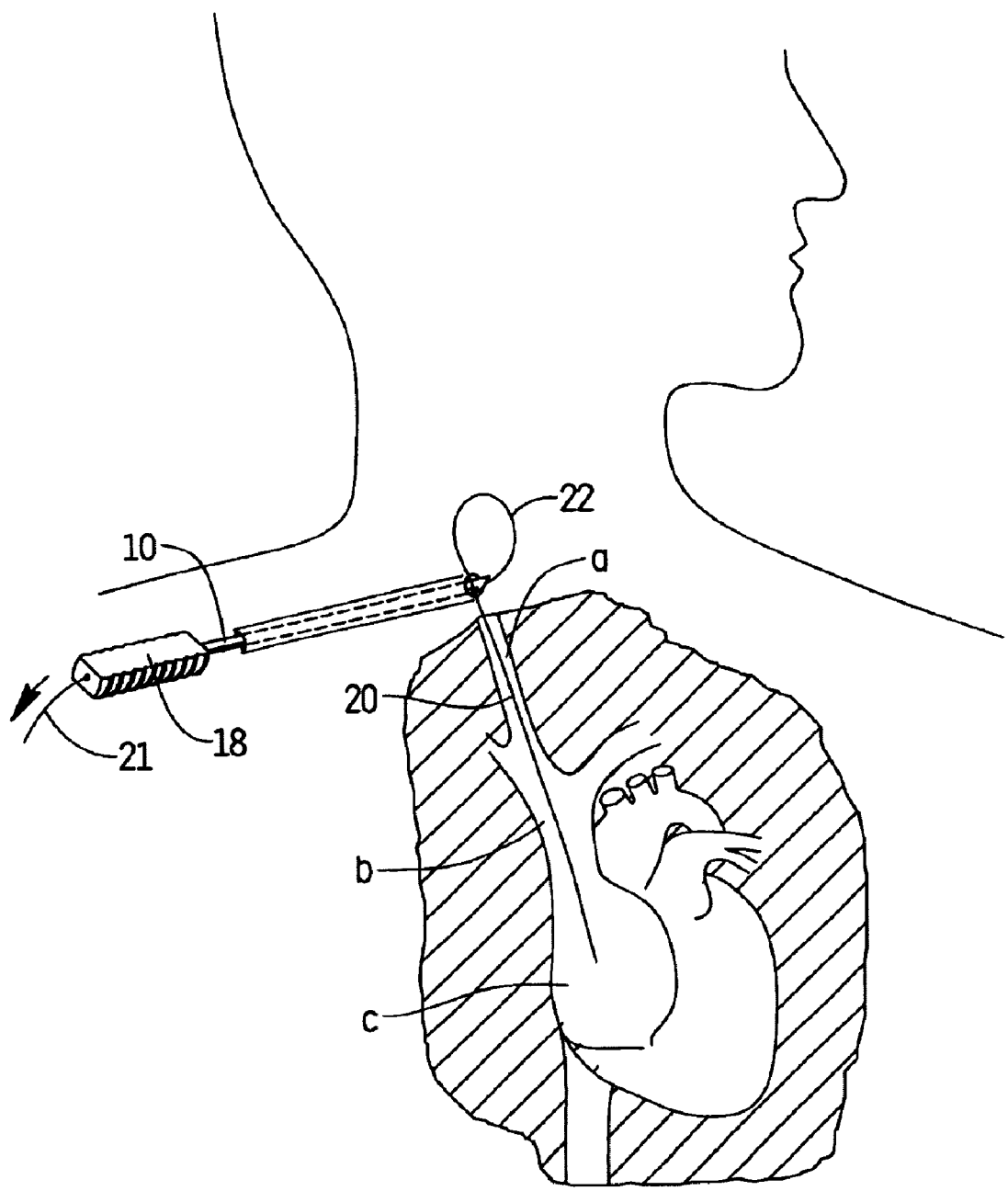

Next, trocar 10 is inserted through a first incision "s" in the patient, bluntly dissecting and tunneling under the skin, and forced out of the tissue at the needle incision site, creating a subcutaneous tunnel "t" under the tissue as shown in FIG. 6B. (A portion of the tunnel (skin) is not shown in FIG. 6B so that the trocar tip can be seen.) This tunnel provides a way to secure the catheter. Guidewire 20 is then threaded through lumen 14 of the trocar, with proximal portion 21 first inserted through trocar distal opening 11 so it emerges out of proximal opening 16 as shown in FIG. 6C. Trocar 10 is then withdrawn from the body in the direction of the arrow of FIG. 6D, leaving the guidewire 20 in place as shown with loop 22. Thus, guidewire 20 extends from the right atrium and superior vena cava, out through the right internal jugular vein and through the tissue tunnel "t", exiting at incision "s".

The catheter, e.g. catheter 30, is then threaded over the guidewire 20, with the proximal portion 21 of the guidewire 20 inserted first through the lumen of the catheter 30, and then advanced through the length of the catheter lumen, and through the hub and into the arterial tube. The catheter 10 is then advanced over the guidewire 20 (FIG. 6F), through the tissue tunnel "t", and exiting incision site "w" into the internal jugular vein "a". The catheter 30, as shown, is formed into a loop 33, tracking the loop 22 of guidewire 20, and then advanced downwardly through the internal jugular vein, the superior vena cava and into the right atrium. The guidewire 20 is then withdrawn, and the catheter 30 is pushed downwardly and/or pulled back to straighten the loop to position the catheter as shown in FIG. 6G. A cuff (not shown) on the catheter 30 is positioned in the tissue tunnel "t" to aid in securement of the catheter by enabling tissue ingrowth over a period of time It should be appreciated that formation of the loop in the guidewire and the catheter is optional and the procedure can be performed without the loop. A dilator can be passed over the guidewire prior to insertion of the catheter over the guidewire to dilate the transition between the two openings.

Note that a stiffening member (not shown in FIGS. 6A–6F for clarity) is preferably utilized, i.e. contained with the catheter lumen and having a longitudinal lumen for insertion over the guidewire 20. The stiffening members are described in detail in the '468 application and further described below.

The catheter can be inserted in a similar fashion through the left internal jugular vein. In this method, the subcutaneous tissue tunnel will be formed on the left side by the trocar 10, and the catheter inserted over the guidewire through the subcutaneous tissue tunnel and through the left internal jugular vein and into the superior vena cava and right atrium in the same way as described for right side insertion. It should be understood that any of the catheters described in the '468 application can be inserted in this fashion as well as through the right internal jugular vein or optionally through the subclavian vein.

In an alternative method of insertion, instead of emerging from the needle-guidewire insertion site, the trocar emerges from a second incision site adjacent the incision site through which the needle and guidewire are introduced into the internal jugular vein. Thus the subcutaneous tissue is formed between the first and second incision. The remainder of the insertion method would be the same.

FIGS. 2A and 2B illustrate an alternate embodiment of the trocar. Trocar 40 is similar to trocar 10 except for an elongated oval entrance opening 42 to lumen 43, formed in the sidewall, for the guidewire and a beveled tip 44 to facilitate tunneling through tissue. The handle configuration 46 is also slightly different as shown.

FIGS. 3A and 3B show another alternate embodiment of a trocar utilized to retrieve the guidewire and pass it through the subcutaneous tissue tunnel. Trocar 50 is similar to trocar 10 of FIG. 1 except for the provision of an opening 52 aligned with the longitudinal axis of the lumen in the distalmost wall 54 of the trocar 50. The trocar could also include, for example, a side channel instead of an internal lumen, for the guidewire.

In the embodiments of FIGS. 1–3, the guidewire is threaded along the length of the longitudinally extending lumen of the trocar, preferably exiting through a proximal opening in the handle. In the alternate embodiments of FIGS. 4, 5A, 5B and 5C (only the distal portion is shown), the guidewire is held by a retaining or engaging structure of the trocar and pulled back through the tunnel as the trocar itself is retracted through the tunnel.

Figure 5C:
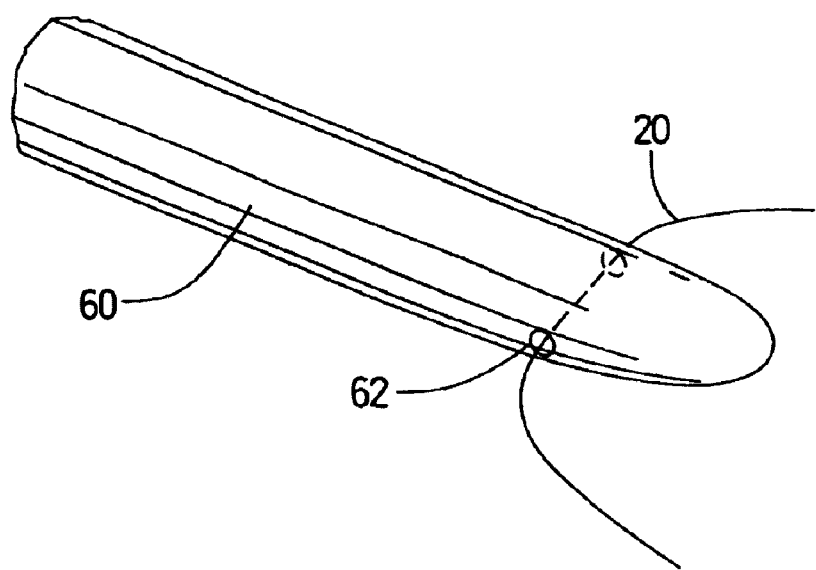
FIG. 5C is a perspective view of a seventh embodiment of the trocar.

In FIG. 5C, trocar 60 has an eyelet 62, formed by two small opposing holes in the sidewalls at the distal end. In FIG. 5B angled cutout 66 in trocar 65 forms a hook 68 to retain guidewire 20. The hook can be formed on the top or the bottom surface. In FIG. 4, guidewire 20 is inserted through a distal opening 72 and is wrapped around cutout 73 in trocar 70. In FIG. 5, trocar 75 has a flexible band 77 through which guidewire 20 is slid under and retained in recess 78 for passage through the tissue tunnel.

It should be understood that instead of the eyelet, a hook or band, other means can be provided on the trocar for holding the guidewire to enable pulling the guidewire through the tissue tunnel.

As noted above, to facilitate insertion, the dialysis catheter is configured to receive a stiffening member in the form of a stiffening rod which stretches the catheter to reduce its profile to aid in over the wire insertion and better navigate through small vessels. The stiffening member thereby enables pushability of the catheter over the wire as described in the '468 application. The stiffening rod is inserted into the central lumen of the catheter; after placement of the catheter, the stiffening rod is removed. A preferred embodiment of the stiffening rod is illustrated in FIG. 8 (see also FIG. 7); two alternate embodiments of the stiffening rods are illustrated in FIGS. 9A and 9B.

In the embodiment of FIG. 9A, stiffening rod 90 has a distal tip 92, a proximal end portion 95 and an internal lumen extending therethrough. Stiffening rod 90 is inserted through the proximal end of an arterial tube (not shown) and over the guidewire 20 (which extends through the lumen) and through the central lumen of the catheter until the distal tip 92 abuts a shoulder or stop in the catheter. The proximal end portion 95 of stiffening rod 90 has a threaded portion 91 which is screwed onto a screw thread of the arterial tube. This temporarily secures the stiffening rod 90 within the catheter during insertion. This threaded mounting requires the stiffening rod 90 to be manually twisted, thereby torquing rod 90 as it presses forwardly and applies a force against shoulder (abutment surface) of the catheter.

After the catheter is positioned at the desired site, the stiffening rod 90 is unthreaded from the proximal thread of the arterial tube and removed from the central lumen of the catheter and from the tube.

In an alternate embodiment of the stiffening rod of FIG. 9B, stiffening rod 100 has a threaded distal end 102 which is threaded onto internal threads of the catheter. A series of proximal threads 101 at proximal end 103 are screwed onto the threads of the arterial tube in the same manner as described above for stiffener rod 90. The stiffening rod 100 functions in the same manner as stiffening rod 90, the only difference being the mechanical threaded attachment of the distal end of the stiffening rod 100 to the catheter.

In the embodiment of FIG. 8, stiffening rod 80 has a thickened wall portion 82 which engages an internal wall in the region 35 of the catheter 30 adjacent the region which contains the cylindrical stiffening insert 37. Since this catheter region is not as flexible, it is not stretched at this region by the stiffener rod 80, thus providing resistance to distal movement of the stiffening rod 80, thereby holding it in place during insertion. The proximal end 87 of the stiffener 80 is threaded onto a luer (not shown) of arterial tubing. The increased wall thickness of stiffener rod 80 cooperates with the distalmost tip 36 of the catheter 30 to prevent coring of tissue during insertion. The stiffener 80 protrudes past the distalmost tip 36 of the catheter body 80 as shown, serving to help dilate tissue during insertion.

It should be appreciated that the foregoing stiffening rods can alternatively be temporarily attached at the proximal end to the arterial tube by other means such as a bayonet lock, snap fit, etc. The stiffening rod could first be manually twisted and then mounted by these various means for retention in its torqued position. The stiffening rods are preferably circular in cross-section, although other configurations are also contemplated.

FIG. 7 illustrates an example of a kit containing a stiffening rod and a trocar. The stiffening rod shown is stiffening rod 80 of FIG. 8 and the trocar illustrated is trocar 40 of FIG. 2A, it being understood that other trocars or stiffeners can be contained in the kit. The kit enables a dialysis catheter, potentially even prior art catheters, to be adapted for over the wire insertion. The user would utilize the trocar to retrieve or access the guidewire and pass it through the subcutaneous tissue tunnel. The user would remove the trocar, leaving the guidewire extending out of the proximal incision of the tunnel. Next, the stiffener rod would be placed within a lumen of the catheter. Utilizing the trocar 80 of the kit in FIG. 7, the thickened wall portion would engage the internal wall of the catheter lumen, to enhance the stiffness and facilitate insertion (pushability) of the catheter over the wire through the tissue tunnel and into the vascular structure of the patient. In this manner, catheters other than those described in the '468 application can be adapted for complete over the wire insertion.

It should also be appreciated that another instrument, other than a trocar, could be used to retrieve the guidewire. For example, after the tunnel is formed by the guidewire, the dilator can be used to retrieve the guidewire. For instance, the guidewire can be inserted through a distal hole in the dilator and pulled through the already formed tissue tunnel. In any event, the guidewire would be passed through the tunnel to enable over the wire insertion of the catheter.

It should also be appreciated that the over the wire insertion method described herein can be utilized for catheters other than dialysis catheters. For example, catheters that communicate with subcutaneously implanted ports and Hickman catheters for injecting chemotherapeutic agents, antibiotics, TPN (total parenteral nutrition), etc. can be placed through the subcutaneous tissue tunnel and over the guidewire that has been passed through the tunnel in the ways described above.

The providing of the guidewire through the subcutaneous tissue tunnel for over the wire insertion of the catheter through the tunnel and into the vessel can also enable, if desired, measurement of the length of catheter required. That is, the guidewire provides a direct path for the catheter through the tunnel and into the vascular system so that the desirable catheter length can be selected prior to insertion. In one version, shown in FIG. 10, the stiffener rod 110 can have indicator markers 112 along its length, preferably at the proximal end, and inserted over the guidewire (through the tunnel and into the vascular system). By utilizing the markings at the proximal end of the stiffener rod, the user can determine the length of the stiffener rod inserted and thus use a catheter of such length. That is, the catheter, for instance, can be trimmed to the desired length corresponding to the length of insertion of the stiffener as indicated by the marker or the marker can be in the form of measurement markers, e.g. centimeters, and the catheter trimmed to a length corresponding to the measurement. Instead of markings, the user can also measure with his fingers the distance the stiffener extends from the tunnel and then use this to determine the catheter length required. Instead of a stiffener rod, other devices such as other dilators can be provided with indicator markings and inserted over the wire and used to determine the length of catheter.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. An apparatus for passing a guidewire through a subcutaneous tissue tunnel to enable over-the-wire insertion of a catheter through the tissue tunnel, the apparatus comprising an elongated member having a distal end portion and an opening, the distal end portion having a tip configured to advance through the tissue tunnel, the opening extending longitudinally with respect to the apparatus and dimensioned to receive the guidewire, the opening extending from the tip of the apparatus to a proximal end portion, wherein the guidewire is inserted through the opening to thereby pass the guidewire through the tunnel to enable subsequent over-the-wire insertion of the catheter.

2. The apparatus of claim 1, wherein the apparatus includes a handle and the opening extends through the handle.

3. An apparatus for passing a guidewire through a subcutaneous tissue tunnel to enable over-the-wire insertion of a catheter through the tissue tunnel, the apparatus comprising an elongated member having a distal end portion and an opening, the distal end portion having a tip configured to advance through the tissue tunnel, the opening extending longitudinally with respect to the apparatus and dimensioned to receive the guidewire, wherein the guidewire is inserted through the opening to thereby pass the guidewire through the tunnel to enable, wherein the opening is formed in a side wall of the apparatus.

4. An apparatus for passing a guidewire through a subcutaneous tissue tunnel to enable over-the-wire insertion of a catheter through the tunnel and into the patient's vessel, the apparatus comprising an elongated member having a distal end portion and guidewire retaining structure, the distal end portion having a tip configured to advance through the tissue tunnel, the guidewire retaining structure engaging the guidewire and retaining the guidewire during movement of the apparatus through the tissue tunnel to thereby enable passage of the guidewire through the tunnel to enable subsequent insertion of the catheter over the guidewire, wherein the guidewire retaining structure includes one of a hook at the distal end portion of the apparatus and a flexible band.

5. A system for placement of a dialysis catheter comprising a trocar and a stiffener, the trocar having a distal tip configured to dissect tissue and an structure to receive a guidewire, the trocar providing passage of the guidewire through a subcutaneous tissue tunnel, the stiffener removably insertable into a lumen of the dialysis catheter to provide increased rigidity to the dialysis catheter to enhance pushability of the dialysis catheter over the guidewire through the tissue tunnel.

6. The system of claim 5, wherein the stiffener comprises a rod having engaging structure abutting an internal wall of the catheter.

7. The system of claim 5, wherein the structure for receiving a guidewire comprises an opening extending along a substantial length of the trocar.

8. The system of claim 7, wherein the stiffener includes a threaded proximal portion for releasable engagement with the dialysis catheter.

9. The system of claim 5, wherein the stiffener includes a longitudinal lumen for receipt of the guidewire.

10. A kit for inserting a dialysis catheter through a subcutaneous tissue tunnel into a patient's vessel, the kit comprising:

a guidewire passer for passing a guidewire through a subcutaneous tissue tunnel so the guidewire extends from the vessel through a proximal opening of the tissue tunnel to enable a dialysis catheter to be inserted through the tissue tunnel over the guidewire; and a stiffener insertable into a lumen of the catheter to stiffen at least a portion of the catheter to facilitate advancement of the catheter over the guidewire through the subcutaneous tissue tunnel and through the vessel.

11. The kit of claim 10, wherein the trocar includes a longitudinal passageway dimensioned to receive the guidewire.

12. The kit of claim 10, wherein the stiffener includes a threaded proximal portion for releasable engagement with the dialysis catheter.

13. The kit of claim 12, wherein the stiffener includes a protruding surface on an outer wall for engagement with an internal wall of the dialysis catheter.

14. The kit of claim 12, wherein the stiffener includes a longitudinal lumen for receipt of the guidewire.

15. The kit of claim 10, wherein the stiffener includes a longitudinal lumen for receipt of the guidewire.

* * * * *